(12) United States Patent
Barber et al.

(10) Patent No.: US 10,296,710 B2
(45) Date of Patent: *May 21, 2019

(54) FAMILY NETWORKS

(71) Applicant: Ancestry.com DNA, LLC, Provo, UT (US)

(72) Inventors: Mathew J. Barber, Chicago, IL (US); Ross E. Curtis, Cedar Hills, UT (US); Catherine Ann Ball, Mountain View, CA (US); Kenneth Gregory Chahine, Park City, UT (US)

(73) Assignee: Ancestry.com DNA, LLC, Provo, UT (US)

( * ) Notice: Subject to any disclaimer, the term of this patent is extended or adjusted under 35 U.S.C. 154(b) by 191 days.

This patent is subject to a terminal disclaimer.

(21) Appl. No.: 15/182,787

(22) Filed: Jun. 15, 2016

(65) Prior Publication Data

US 2016/0300012 A1    Oct. 13, 2016

Related U.S. Application Data

(63) Continuation of application No. 14/214,856, filed on Mar. 15, 2014, now Pat. No. 9,390,225.

(Continued)

(51) Int. Cl.
*G06F 19/00* (2018.01)
*G06F 19/14* (2011.01)
(Continued)

(52) U.S. Cl.
CPC .......... *G06F 19/14* (2013.01); *G06F 16/2246* (2019.01); *G06F 16/248* (2019.01);
(Continued)

(58) Field of Classification Search
CPC .......... G06F 19/18; G06F 19/22; G06F 19/24; G06F 19/14; G06F 19/28;
(Continued)

(56) References Cited

U.S. PATENT DOCUMENTS 8,463,554 B2   6/2013   Hon et al.
8,855,935 B2   10/2014  Myres et al.
(Continued)

FOREIGN PATENT DOCUMENTS

EP      2370929 A1       10/2011
EP      3276526 A1       1/2018
WO   WO 2010/077336 A1   7/2010

OTHER PUBLICATIONS

Glodzik, D. et al. European Journal of Human Genetics (Jan. 2013) vol. 21, pp. 1140-1145.

(Continued)

*Primary Examiner* — Mary K Zeman
(74) *Attorney, Agent, or Firm* — Fenwick & West LLP (57) ABSTRACT

Described embodiments enable identification of family networks using combinations of DNA analysis and genealogical information. Genealogical data is provided by users of a genealogical research service or collected from other sources and used to create family trees for each user. DNA samples are also received from the users. By analyzing the DNA samples, potential genetic relationships can be identified between some users. Once these DNA-suggested relationships have been identified, common ancestors can be sought in the respective trees of the potentially related users. Where these common ancestors exist, an inference is drawn that the DNA-suggested relationship accurately represents a familial overlap between the individuals in question. People descended from the same common ancestor are each members of a family network. Members of a family network not in a user's tree may be identified for the user, enabling the user to discover additional ancestors that might otherwise have remained unknown.

24 Claims, 8 Drawing Sheets

Related U.S. Application Data (60) Provisional application No. 61/786,398, filed on Mar. 15, 2013.

(51) Int. Cl.

| | |
|---|---|
| *G06F 16/248* | (2019.01) |
| *G06F 16/25* | (2019.01) |
| *G06F 16/22* | (2019.01) |
| *G06F 16/2457* | (2019.01) |
| *G06F 17/30* | (2006.01) |
| *G09B 19/00* | (2006.01) |

(52) U.S. Cl.
CPC ...... *G06F 16/24575* (2019.01); *G06F 16/252* (2019.01); *G06F 17/3056* (2013.01); *G06F 17/30327* (2013.01); *G06F 17/30528* (2013.01); *G06F 17/30554* (2013.01); *G09B 19/0046* (2013.01)

(58) Field of Classification Search
CPC ......... G06F 17/30958; G06F 17/30292; G06F 17/30327; G06F 17/30554; G06F 19/20; G06F 19/34; G06F 17/241; G06F 17/30598; G06F 17/30979; G06F 19/26; G06F 17/30038; G06F 17/30312; G06F 17/30572; G06F 17/30595; G06F 17/30604; G06F 17/3061; G06F 17/30867; G06F 17/30908; G06F 2216/03; G06F 3/048; G06F 3/04842
See application file for complete search history.

(56) References Cited

U.S. PATENT DOCUMENTS

| | | | |
|---|---|---|---|
| 9,390,225 B2 * | 7/2016 | Barber | G06F 19/14 |
| 2002/0032687 A1 | 3/2002 | Huff | |
| 2005/0147947 A1 | 7/2005 | Cookson, Jr. et al. | |
| 2005/0267903 A1 * | 12/2005 | Golze | G06Q 10/10 |
| 2006/0025929 A1 | 2/2006 | Eglington | |
| 2007/0178500 A1 | 8/2007 | Martin et al. | |
| 2008/0027656 A1 * | 1/2008 | Parida | G06F 19/14 |
| | | | 702/20 |
| 2008/0081331 A1 | 4/2008 | Myres et al. | |
| 2008/0189047 A1 * | 8/2008 | Wong | G06F 19/14 |
| | | | 702/20 |
| 2010/0223281 A1 | 9/2010 | Hon et al. | |
| 2014/0006433 A1 | 1/2014 | Hon et al. | |
| 2014/0025308 A1 * | 1/2014 | Jorde | G06F 19/18 |
| | | | 702/19 |
| 2017/0228498 A1 | 8/2017 | Hon et al. | |
| 2017/0329891 A1 | 11/2017 | Macpherson et al. | |

OTHER PUBLICATIONS

Huff, C. D. et al. Genome Research (2011) vol. 21 No. 5 pp. 768-774.
Li, X. et al. Bioinformatics (2010) vol. 26 No. 12 p. i191-i198.
Gusev, A. et al., "Whole Population, Genome-wide Mapping of Hidden Relatedness," Genome Research, 2008, pp. 318-326.
PCT International Search Report, PCT Application No. PCT/US2014/030014, dated Jul. 11, 2014, 3 pages.
PCT Written Opinion, PCT Application No. PCT/US2014/030014, dated Jul. 11, 2014, 4 pages.
New Zealand First Examination Report, New Zealand Application No. 629509, dated Nov. 10, 2015, 3 pages.
Canadian Office Action, Canadian Application No. 2,906,180, dated Sep. 12, 2016, 4 pages.
New Zealand Second Examination Report, New Zealand Application No. 629509, dated Oct. 6, 2016, 3 pages.
Canadian Office Action, Canadian Application No. 2,906,180, dated Jun. 21, 2017, 4 pages.
European Extended Search Report, European Application No. 14762682.4, dated Oct. 27, 2016, 9 pages.
Canadian Office Action, Canadian Application No. 2,906,180, dated Jul. 24, 2018, 3 pages.

* cited by examiner

FAMILY NETWORKS

CROSS-REFERENCE TO RELATED APPLICATIONS

This application is a continuation of U.S. application Ser. No. 14/214,856, filed Mar. 15, 2014, now U.S. Pat. No. 9,390,225, which application claims the benefit of U.S. Provisional Application 61/786,398, filed Mar. 15, 2013, all of which are incorporated by reference in their entirety.

BACKGROUND

Field

This disclosure relates generally to computer software for identification of family relationships based on combinations of DNA matching and genealogical records.

Description of Related Art

Genealogical research is typically undertaken by individuals interested in learning more about their family history. Generally, researchers build their family trees by entering information about known ancestors, including, for example, birth and death dates and locations, spouses, offspring, and the like. Software designed for genealogical research is often used for this purpose, and may be used in a standalone fashion, or via a networked implementation. Some genealogical research services offer suggestions to researchers about additional information that may be available about relatives already present in their family trees such as census information, immigration records, etc.

Services also exist for extracting and characterizing DNA samples from individuals. Some services identify similar DNA segments between customers and suggest to the customers having those similar segments that they may be related.

SUMMARY

Described embodiments enable identification of family networks using combinations of DNA analysis and genealogical information. Genealogical information is provided by users of a genealogical research service or collected from other sources and used to create family trees for each of the users. DNA samples are also received from the users and analyzed. By comparing the results of the DNA analysis, potential genetic relationships can be identified between some users. Once these DNA-suggested relationships have been identified, common ancestors can be sought in the respective family trees of the potentially related users. Where these common ancestors exist, an inference is drawn that the DNA-suggested relationship accurately represents a familial overlap between the individuals in question.

People descended from a common ancestor are each members of a family network, though no single genealogical tree compiled by a single user may yet include all of the members of the network. In various embodiments, members of a family network not in a user's tree may be identified for the user. In this way, a user can discover additional ancestors that might otherwise have remained a mystery.

DETAILED DESCRIPTION

Figure 1:
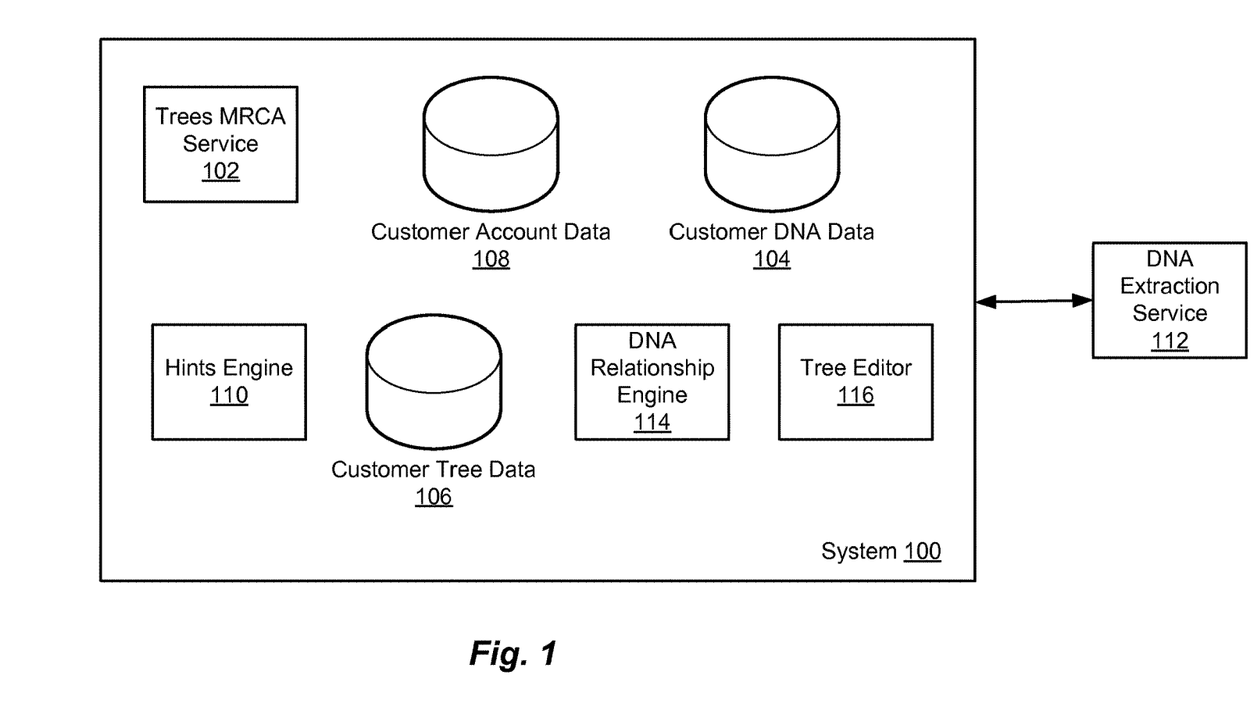
FIG. 1 is a block diagram illustrating components of a system for identifying family networks in accordance with one embodiment.

FIG. 1 illustrates an example system 100 for identifying family networks in accordance with one embodiment. System 100 includes a trees most recent common ancestor (MRCA) service 102, customer DNA data store 104, customer trees data store 106, customer account data store 108, hints engine 110, a DNA relationship engine 114, and tree editor 116. FIG. 1 also illustrates a DNA extraction service 112. Each of these elements is described further below.

For purposes of clarity within this description, we assume that system 100 is administered by or on behalf of a company providing genealogical research services to its customers, though many other use cases will be apparent from the disclosure. One example of such a company is Ancestry.com, of Provo, Utah. Services may be provided to customers via the web, in person, by telephone, by mail, or various combinations of the above.

Figure 2:
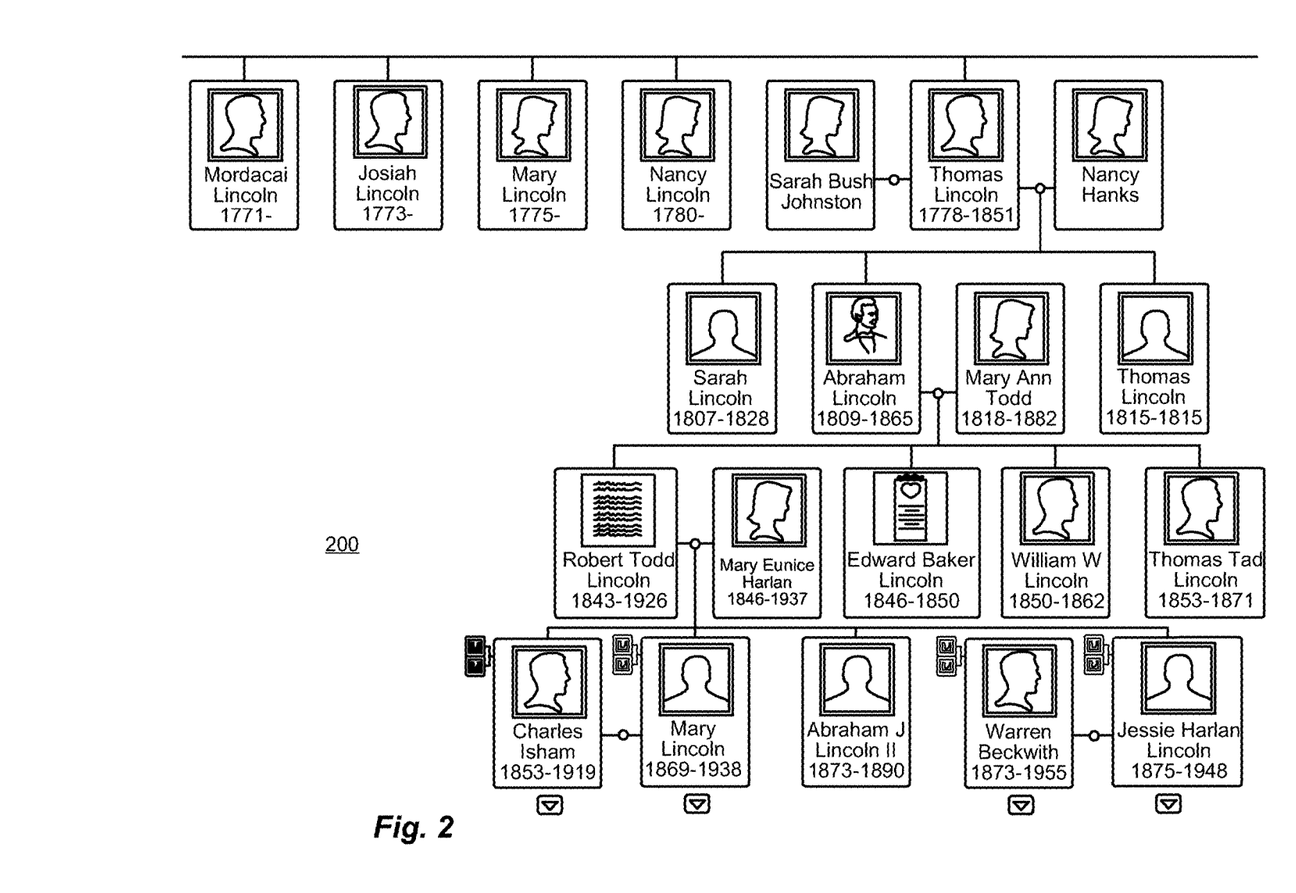
FIG. 2 illustrates a portion of a family tree in accordance with one embodiment.

Customers of system 100 (which we also refer to interchangeably as "users") have accounts with system 100, and account data in various embodiments is stored in customer account data store 108. Customers may create family trees containing genealogical data known to the customer or obtained by the customer from the genealogical research service. For example, tree editor 116 in various embodiments includes a web interface through which users can enter or upload genealogical data using their computers or mobile devices. System 100 stores tree data for a customer in customer tree data store 106. In various embodiments, trees include records describing individuals that are thought by the curator of the tree (e.g., the user) to be related. Each record may include, for example, an individual's name, date of birth, date of death, birth and death locations, places lived, education, and other information known about the individual. In addition, the record describes connections between the individual and other people in the tree, for example by describing the individual's parents, siblings, spouses and children. In various embodiments, these connections are links or pointers to other individual records in the same tree. Records, which are stored in customer tree data store 106, may be added, deleted or modified as desired by curators of the tree. For example, FIG. 2 illustrates a portion of a family tree 200 of Abraham Lincoln (1809-1865). Duplicate records for any particular individual may exist in customer trees data store 106 as a consequence of different users creating independent records for the same individual in their respective family trees—for example, two users of system 100 may be related to each other as third cousins, and each may have a family tree that includes their great-great-grandfather—an ancestor common to both cousins. As described below, these multiple records describing a single individual, when combined with DNA-suggested relationships, lead to the discovery and expansion of family networks.

In addition to providing genealogical data to populate family trees, customers of system 100 may also provide DNA samples for analysis of their genetic data. In one embodiment, a customer obtains a sample collection kit associated with his account in customer account data store 108. The customer uses the sample collection kit to provide a sample, e.g., saliva, from which genetic data can be reliably extracted according to conventional methods. DNA extraction service 112 receives the customer sample and genotypes the genetic data, for example by extracting the DNA from the sample and identifying values of single nucleotide polymorphisms (SNPs) present within the DNA. In one embodiment, genotyping takes place at a large number, e.g., 700,000 SNP locations in the genome. In various embodiments, inferences about the customer may be made using the SNP data, for example including a prediction of the customer's ethnic background and the geographic migration patterns of the customer's ancestors. System 100 receives the genetic data from DNA extraction service 112 and stores the genetic data in customer DNA data store 104 along with an association to the customer account in customer account data store 108.

Note that in various embodiments, depending on the information a particular customer has chosen to provide, the customer may have family tree data stored in customer tree data store 106, genetic data stored in customer DNA data store 104, or both.

DNA relationship engine 114 analyzes the genetic data contributed by customers and stored in DNA data store 104 to identify potential genetic relationships between the customers. In one embodiment, the GERMLINE algorithm is used to identify shared segments of genotype data between users. The GERMLINE algorithm is described in Gusev A, Lowe J K, Stoffel M, Daly M J, Altshuler D, Breslow J L, Friedman J M, Pe'er I (2008) *Whole population, genomewide mapping of hidden relatedness*, Genome Research, and is incorporated by reference herein in its entirety.

Each potential genetic relationship identified by DNA relationship engine 114 is noted in the customer account data for each of the potentially matching customers if the potential genetic relationship is significant. The threshold level for a significant genetic relationship is set depending on the preference of the implementer. In various embodiments, a potential genetic relationship between two customers is identified by DNA relationship engine 114 as significant if a significant similarity exists at the same part of their genomes, for example, in one embodiment at least $5*10^6$ continuous base pairs are identical between two individuals. Other thresholds may be set according to the preference of the implementer. We refer in this disclosure to two or more customers for whom an identification of a significant genetic relationship has been made as "DNA suggested relations." In various embodiments, a confidence score indicating the degree of genetic similarity between the DNA suggested relations is calculated and stored in the customer account data.

Family Network Identification

A group of people, each descended from a particular common ancestor for whom a record exists in customer tree data store 106 (and including the ancestor's record) constitutes a family network. In some embodiments, a family network is further limited to include only those people who descend according to customer tree data from a common ancestor and who are also DNA suggested relations with at least one other member of the tree based on data stored in DNA data store 104.

For any group of two or more people having records in tree data store 106, we refer to their closest common ancestor(s) from a generational perspective as their "most recent common ancestor(s)" or MRCA. For example, referring again to the family tree in FIG. 2, the most recent common ancestors of Jessie Harlan Lincoln and Thomas Tad Lincoln are Abraham Lincoln and his wife Mary Ann Todd. More formally, in one embodiment for any two people, their MRCAs are the people from whom they are directly descended and for whom no other person from whom they are directly descended is generationally closer.

Figure 3:
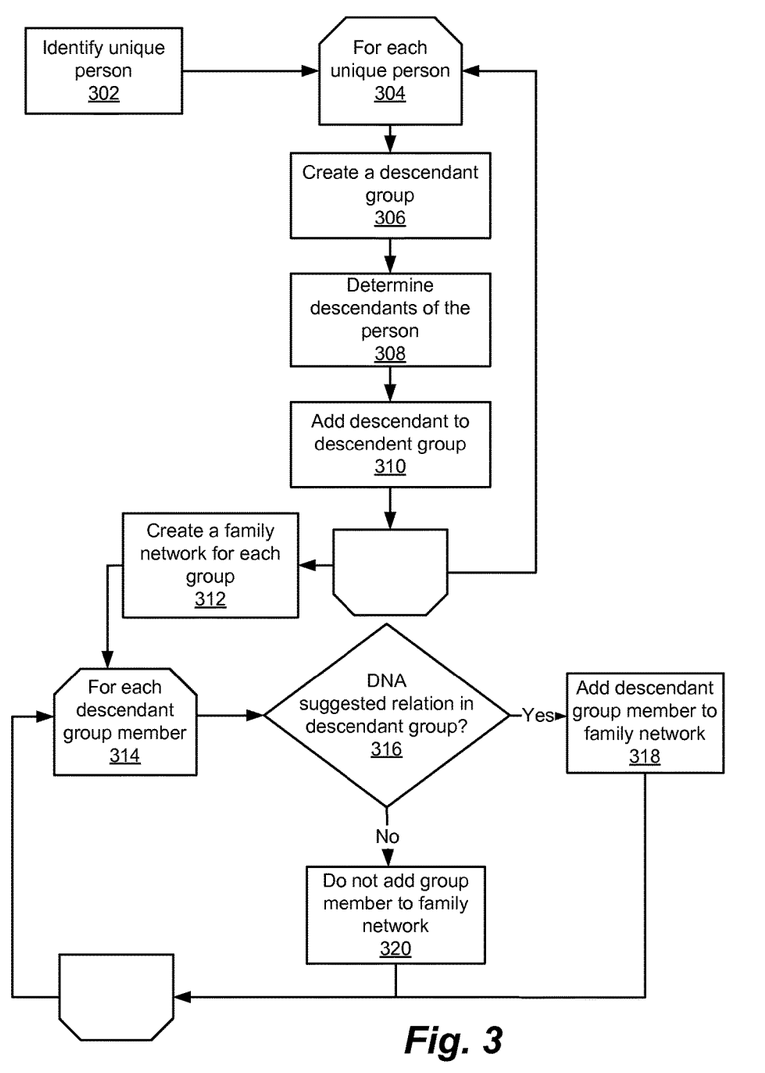
FIG. 3 is a flowchart illustrating a method for creating family networks in accordance with one embodiment.

In one embodiment, and referring now to FIG. 3, family networks are identified as follows. Trees MRCA service 102 examines each record in customer tree data 106 to identify 302 each unique person. That is, a particular person may be named in multiple trees as described above—for example if many different users have an instance of the same person in each of their trees—and therefore be represented by multiple records, but be in fact a unique individual. Multiple instances of a single individual in various embodiments are identified by comparing names, birth dates, death dates, places of residence and other bibliographic data to establish a likelihood that any two or more records in fact describe the same individual. For each unique person identified 304, MRCA service 102 creates 306 a descendant group and identifies 308 all known descendants of that unique individual across all customer trees in tree data store 106. Each descendant is then added 310 to the descendant group for the unique individual. MRCA service 102 repeats the process for each unique individual.

At least one family network is created 312 for each descendant group. In one embodiment, at the conclusion of steps 302-310 each descendant group anchored by the unique individual, e.g., the unique common ancestor, is designated as a family network. In another embodiment, and still referring to FIG. 3, each descendent group member in a descendant group is evaluated 314 to determine whether 316 that descendent group member has a DNA-suggested relation who is also in the descendant group. If so, the descendant group member 318 is added to the family network anchored by the unique individual. Otherwise, the descendent group member is not added 320 to the family network. In this embodiment, a family network includes only a common ancestor and individuals who are shown to be related via both genealogical and genetic data and is more likely to exclude tree members who were added incorrectly, for example through errors in the curation of the genealogical data.

Figure 4:
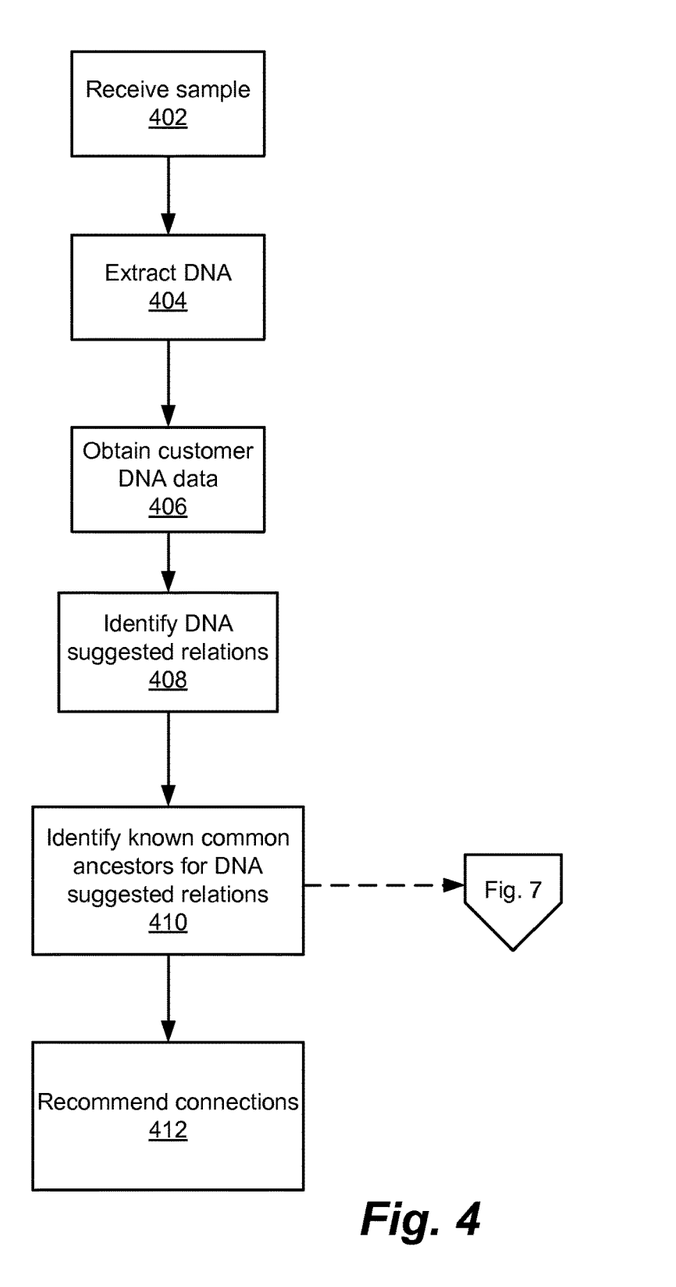
FIG. 4 illustrates a method for creating family networks in accordance with one embodiment.

In various alternative embodiments, family networks are created by using DNA-suggested relationships to search for most recent common ancestors. FIG. 4 illustrates a method for creating family networks in accordance with one such alternative embodiment. Genetic data is obtained, for example by receipt 402 of a customer saliva sample, and DNA is extracted 404 from the sample by DNA extraction service 112 as described above. Genetic data is obtained 406 from the DNA and stored in customer DNA data store 104. DNA relationship engine 114 uses genetic data 406 across multiple customer DNA data store 104 to identify 408 DNA-suggested relations as described above.

For each of the users in a pair of DNA-suggested relations, hints engine 110 searches the users' respective trees in tree data store 106 to locate 410 within the trees one or more potential common ancestors. As described above with respect to FIG. 3, common ancestors with instances in both trees may be identified by comparing names and other bibliographic data to establish a likelihood that any two individuals are in fact the same person. Hints engine 110 then creates a hint including indicia of the records from each tree for the potential match. Indicia may include, for example, a record identifier for the record.

Figure 5:
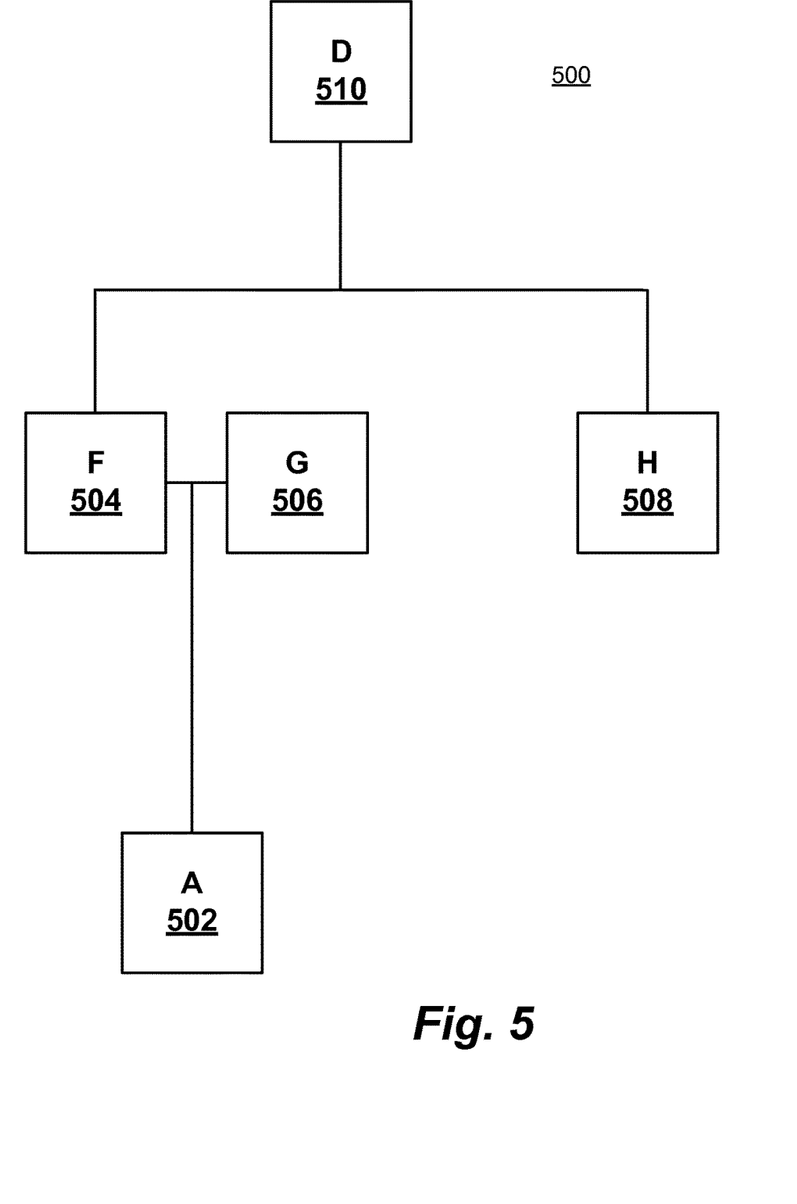
FIG. 5 illustrates a portion of a family tree in accordance with one embodiment.
Figure 6:
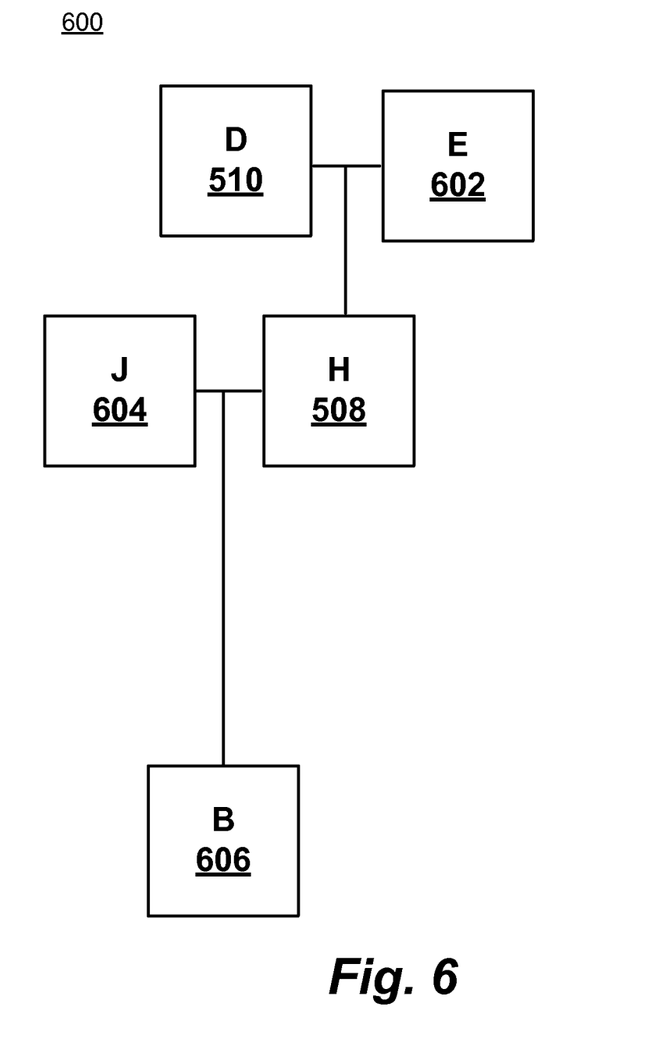
FIG. 6 illustrates a portion of a family tree in accordance with one embodiment.

For example, referring to FIG. 5, consider a family tree 500 that includes four people—D 510, D's children F 504 and H 508, F's spouse G 506, and A 502, the child of F and G. A second family tree 600 is illustrated in FIG. 6. This second tree also includes person D 510 and person H 508, and additionally includes D's spouse E 602; H's spouse J 604; and B 606, the child of H and J.

As can be seen from the two trees above when viewed together, D 510 is a common ancestor of A 502 and B 606, though this is not apparent from either of the trees when considered individually.

Assume that both tree 500 and tree 600 are stored in tree data store 106. Assume also that individuals A 502 and B 606 have submitted DNA samples and been identified as DNA-suggested relations.

Hints engine 110 identifies A and B as DNA-suggested relations and searches their respective trees 500 and 600 for instances of common ancestors as described above with respect to FIG. 4. Since individual D 510 is in both tree 500 and tree 600—that is, D is a common ancestor, hints engine 110 creates a hint with indicia of both records. For example:

Hint#1: (D, Tree1); (D', Tree2).

The notation D and D' illustrates for purposes of this disclosure two distinct records in trees data store 106 that each refer to the same unique individual.

If individual E (married, in this example, to D, though not illustrated in FIG. 5) also exists in both trees, hints engine 110 identifies a second hint:

Hint #2: (E, Tree1); (E', Tree2).

Figure 7:
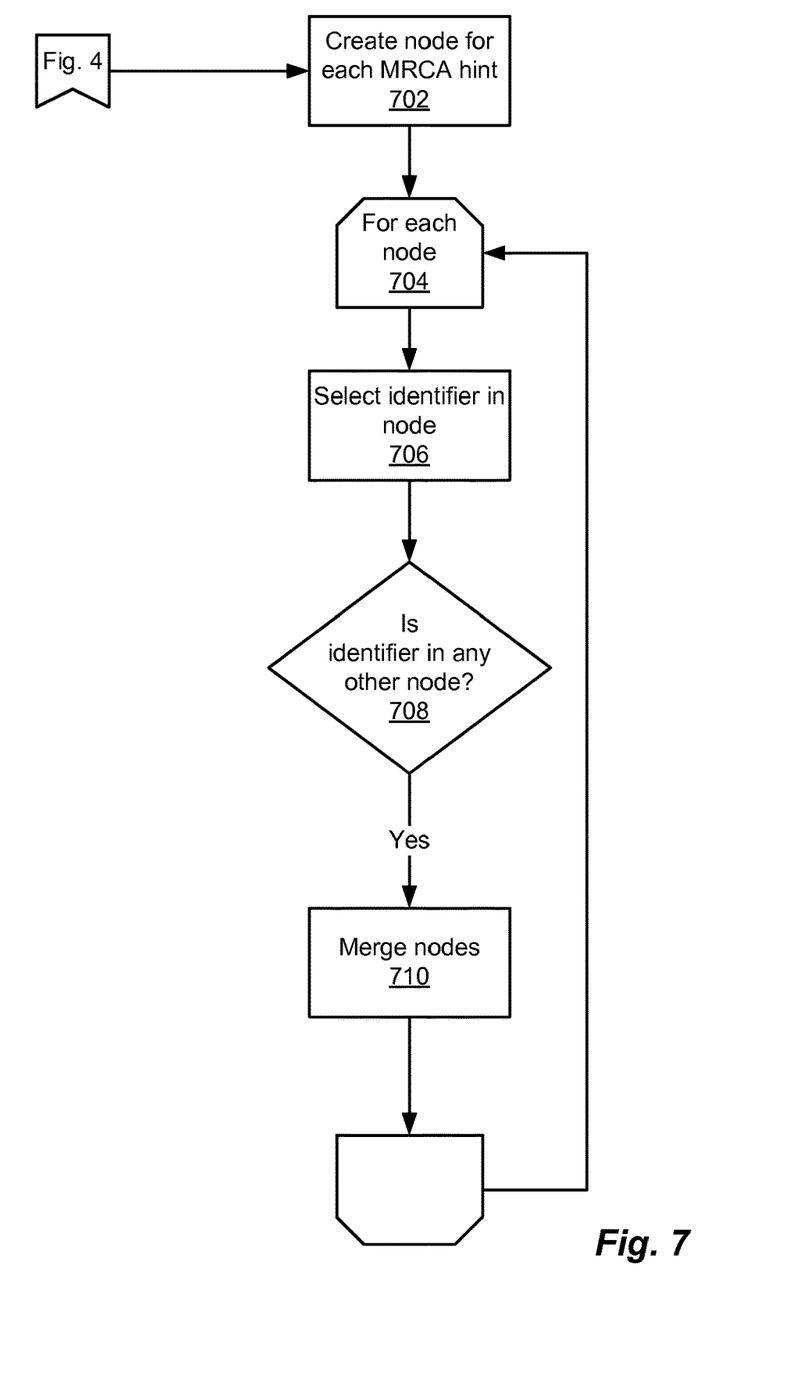
FIG. 7 illustrates a method for collapsing nodes in accordance with one embodiment.

Referring now to FIG. 7, each hint for a most recent common ancestor (MRCA) can be considered a node for a common ancestor. Hints engine 110 therefore can create 702 two nodes in the above example:

Node #1: (D, Tree1; D', Tree2).
Node #2: (E, Tree1; E', Tree2).

Once hints engine 110 has created all possible nodes across all trees for all individuals with DNA-suggested relationships, each node can be further collapsed 704. For example, beginning with Node #1, the record D, Tree1 may exist in another node, such as one associated with another DNA-suggested relation of user A:

Node #3: (D, Tree1, D", Tree3).

Hints engine 110 then merges the nodes:

Node #1: (D, Tree1; D', Tree2; D", Tree3).

Thus, for each node 704, hints engine 110 selects 706 an identifier in the node and determines 708 whether the identifier is present in another node. If so, the nodes are merged 710. By iterating over all nodes, a concatenated set of nodes is created. Within each node, all of the records point to different instances in different trees of the same person, i.e. the common ancestor of the concatenated set of DNA-suggested relations. The common ancestor combined with the DNA-suggested relations together constitute a family network. In one embodiment, hints engine 110 updates the records for each of the members of the family network to reflect this finding. In an alternative embodiment, hints engine 110 recommends 412 (FIG. 4) the addition of the family network members to each user, leaving to the user the option of adding one or more of the recommended relatives to the user's tree.

In various embodiments, the analysis described above is run once at set up time, and then periodically thereafter. In addition, or alternatively, the analysis is repeated when one or more new DNA samples are received by customer DNA data store 104.

When one or more customers are identified as part of a family network, in various embodiments system 100 notifies the customers of the finding. This may include, for example, introducing DNA-suggested relations within the family network to one another; or identifying ancestors earlier than the most recent common ancestor who may be missing from trees of some members of the family network.

One or more customers identified by DNA relationship engine 114 as having a sufficient genetic similarity to indicate a possible relationship may not yet have a family tree in customer tree data store 106 complete enough to see common ancestors. For example, the customer may not have any tree at all (and so no common ancestor will be seen between the customer and the other users in the database).

An opportunity exists to enable the customer without a sufficient tree for explicit identification of common ancestors to begin building their tree using the identified common ancestor(s) from the other customers' trees. For example, referring again to FIG. 2, if a customer is identified as a DNA-suggested relation of Mary Lincoln (1869-1938), Abraham J Lincoln II (1873-1890) and Jessie Harlan Lincoln (1875-1948), each of whom has a known common ancestor in Robert Todd Lincoln (1843-1926), then hints engine 110 can suggest that Robert Todd Lincoln should be in the new customer's family tree.

In some embodiments a confidence score is used to determine whether or not the number of matches between a customer and a family network is significant. For example, a high-confidence hint for a customer would result if a customer had eight DNA-suggested relations in a family network of size eight. One method for estimating a confidence level is to create a score based on either or both of two factors: the total number of people in each family network—e.g., five DNA-suggested relations in a family network of size six is more significant than five DNA-suggested relations in a family network of size eight; and the total number of matches a customer has—e.g., four DNA-suggested relations in a family network of size six is more significant if that customer only has 100 DNA-suggested relations rather than 10,000. By adapting to these factors, the score is broadly comparable (on approximately the same scale) across all family networks and all customers. In constructing family networks as described above, if the probability of observing the identified number of DNA-suggested relations in a family network is small, then that family network is significant, and suggests to a meaningful level of confidence that the customer is related to the family network through a mutual common ancestor.

We begin with the assumption that a customer's DNA will on occasion match some members of a random family network to whom the customer is not closely related—for example, because of false matching, relationships through another unrelated line, relationship between members of the family network, or the like. The confidence score therefore reflects a determination that the number of matches (to a family network) identified is more significant than a random occurrence. A simple binomial sampling model or another statistical model is used (valid only under various approximately true assumptions) to calculate a coarse probability of observing at least that many of the DNA customer's DNA-suggested relations in that family network. A simple transformation of the coarse probability is the quantitative score that hints engine 110 uses to measure interest level between a customer and a family network. In one embodiment, hints engine 110 estimates a level of confidence in a family network hint using a single quantitative score.

To increase the degree of confidence in the score that other individuals should also belong to that family network, in various embodiments system 100 also considers birth locations in the tree, known surnames in the tree, and the strength of DNA matches to the descendants in the network.

In one embodiment, hints engine 110 uses DNA suggested relations to hint to a customer information to help her build her family tree stored in the customer trees data store 106. In this embodiment, hints engine 110 provides suggestions to the customer of specific places and surnames where her family might have lived.

Consider, for example, a customer with multiple distant DNA suggested relations stored in customer DNA data 104. By considering the DNA suggested relations that have trees in customer trees data store 106, hints engine 110 can identify counties, surnames, or other information that is common across a customer's DNA suggested relation's trees. To normalize these counts, hints engine 110 creates a normalization set that includes the total count of all counties, surnames, or other information of interest. In some embodiments, this information can be aggregated across all parts of the trees, or it can be limited to specific time periods of interest.

For example, consider a customer who does not have a tree. By aggregating information across m DNA suggested relations for this customer, hints engine 110 finds that Allegheny County, Pa. is found in the tree of k DNA suggested relations. In the normalization set, Allegheny County is found in L customer trees. Given n, the total number of DNA customers with data in customer DNA data store 104, hints engine 110 can use a statistical model to determine the significance of observing k instances of Allegheny County in m matches. In one embodiment, the binomial distribution is used with parameters p and m, where p is equal to L/n. If Allegheny County is found to be significant, it is given to the customer as a hint to where that customer's family might have lived.

Figure 8:
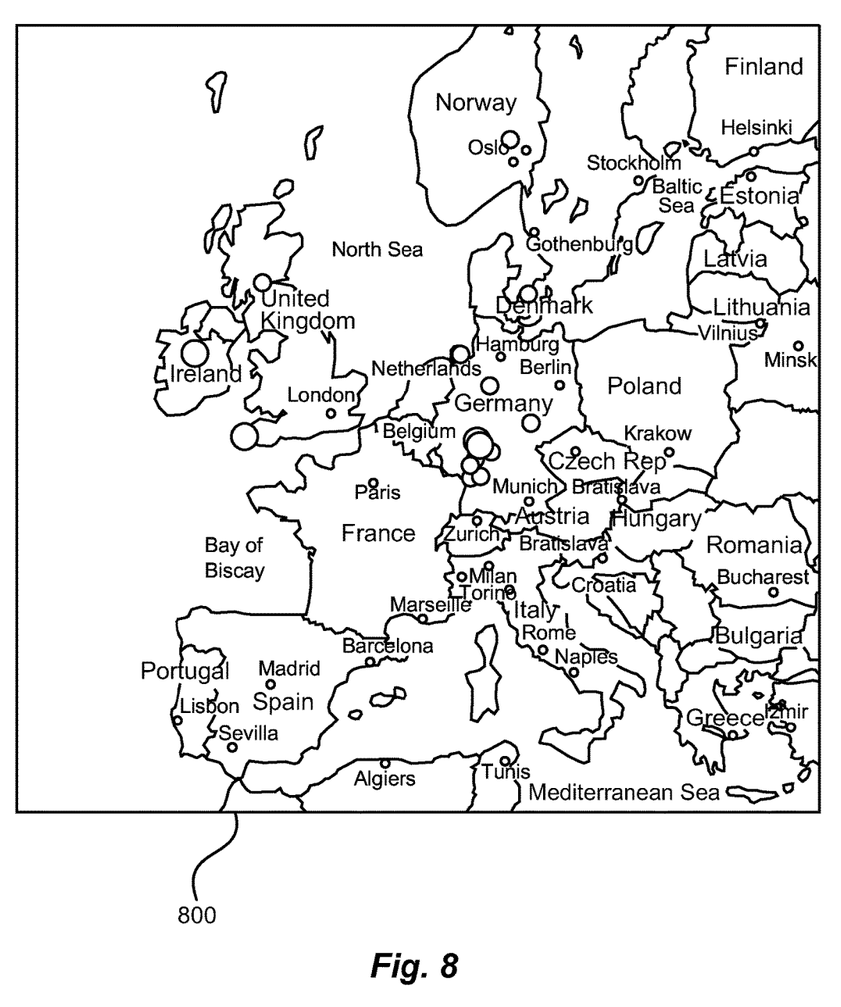
FIG. 8 illustrates an example of a user interface illustrating birth locations of a customer's DNA suggested relations in accordance with one embodiment.

Hints engine 110 delivers the significant information to the customer in one embodiment in the form of tree-building hints. In one embodiment, the hints engine delivers a list of the top five surnames that the customer might expect to find in her tree. In another embodiment, and referring to FIG. 8, hints engine 110 renders a map view 800 illustrating a number of countries of birth for a customer's DNA suggested relations born during certain time periods. In another embodiment, the customer views the locations on the map to get a general feel for where their family has lived, suggesting counties in which to search for records.

In addition to the embodiments specifically described above, those of skill in the art will appreciate that the invention may additionally be practiced in other embodiments. For example, in an alternative embodiment, DNA extraction service 112 is part of system 100.

Although this description has been provided in the context of specific embodiments, those of skill in the art will appreciate that many alternative embodiments may be inferred from the teaching provided. Furthermore, within this written description, the particular naming of the components, capitalization of terms, the attributes, data structures, or any other structural or programming aspect is not mandatory or significant unless otherwise noted, and the mechanisms that implement the described invention or its features may have different names, formats, or protocols.

Further, some aspects of the system may be implemented via a combination of hardware and software or entirely in hardware elements. Also, the particular division of functionality between the various system components described here is not mandatory; functions performed by a single module or system component may instead be performed by multiple components, and functions performed by multiple components may instead be performed by a single component. Likewise, the order in which method steps are performed is not mandatory unless otherwise noted or logically required.

Unless otherwise indicated, discussions utilizing terms such as "selecting" or "computing" or "determining" or the like refer to the action and processes of a computer system, or similar electronic computing device, that manipulates and transforms data represented as physical (electronic) quantities within the computer system memories or registers or other such information storage, transmission or display devices.

Electronic components of the described embodiments may be specially constructed for the required purposes, or may comprise one or more general-purpose computers selectively activated or reconfigured by a computer program stored in the computer. Such a computer program may be stored in a computer readable storage medium, such as, but is not limited to, any type of disk including floppy disks, optical disks, DVDs, CD-ROMs, magnetic-optical disks, read-only memories (ROMs), random access memories (RAMs), EPROMs, EEPROMs, magnetic or optical cards, application specific integrated circuits (ASICs), or any type of non-transitory media suitable for storing electronic instructions, and each coupled to a computer system bus.

Finally, it should be noted that the language used in the specification has been principally selected for readability and instructional purposes, and may not have been selected to delineate or circumscribe the inventive subject matter. Accordingly, the disclosure is intended to be illustrative, but not limiting, of the scope of the invention.

We claim:

1. A computer-implemented method for identifying genealogically related individuals, the method comprising:

maintaining a plurality of sets of genetic data sampled from a plurality of human individuals;

receiving a set of genetic data sampled from a first human individual not included in the plurality of human individuals;

identifying segments of genetic data shared between the received set of genetic data and one or more of the maintained sets of genetic data, the segmental sharing indicating that one or more human individuals corresponding to the one or more sets, including a second human individual, are genetically related to the first human individual;

accessing a first set of genealogical data representing ancestors of the first human individual;

accessing a second set of genealogical data representing ancestors of the second human individual;

creating, by a computer, a first set of nodes where each node in the first set corresponds to a unique individual present in the first set of genealogical data, each node comprising an identifier corresponding to a location of the unique individual within the first set of genealogical data;

creating, by a computer, a second set of nodes where each node in the second set corresponds to a unique individual present in the second set of genealogical data, each node comprising an identifier corresponding to a location of the unique individual within the second set of genealogical data, the first and second sets of nodes having at least one unique individual in common;

concatenating, by the computer, the first set of nodes with the second set of nodes to create a concatenated set of nodes, the concatenating comprising merging nodes both comprising a same identifier;

selecting, by the computer from one of the nodes in the concatenated set, a common ancestor of the first human individual and the second human individual; and providing, by the computer, bibliographic data about the common ancestor to the first human individual.

2. The method of claim 1 wherein the set of genetic data received from the first human individual includes values of single nucleotide polymorphisms present within DNA of the first human individual.

3. The method of claim 1 wherein identifying shared segments of genetic data between the indicated one or more human individuals and the first human individual further comprises:
identifying a length of the shared segments of genetic data, wherein the length of the shared segments is a number of continuous based pairs that are identical between individuals; and
determining that the length of the shared segments exceeds a threshold length.

4. The method of claim 1 wherein the first set of genealogical data describes familial relationships of the first human individual received from the first individual and the second set of genealogical data describes familial relationships of the second human individual received from the second individual.

5. The method of claim 4 further comprising:
identifying by the computer, based on the described familial relationships of the first set of genealogical data, an additional individual identified in the first set of genealogical data genealogically related to the second human individual, the additional individual not identified in the second set; and
providing, by the computer, information about the additional individual to the second human individual.

6. The method of claim 5 further comprising:
adding, by the computer, a record indicator of the additional individual to the second set of genealogical data in response to a request from the second individual.

7. The method of claim 1 wherein the bibliographic data includes places of residence of the individuals.

8. The method of claim 1 wherein the first human individual and the second human individual were unknown to each other prior to the step identifying segments of genetic data.

9. A non-transitory computer readable storage medium comprising computer program instructions that, when executed by a processor of a computer, cause the processor to:
maintain a plurality of sets of genetic data sampled from a plurality of human individuals;
receive a set of genetic data sampled from a first human individual not included in the plurality of human individuals;
identify segments of genetic data shared between the received set of genetic data and one or more of the maintained sets of genetic data, the segmental sharing indicating that one or more human individuals corresponding to the one or more sets, including a second human individual, are genetically related to the first human individual;

access a first set of genealogical data representing ancestors of the first human individual;

access a second set of genealogical data representing ancestors of the second human individual;

create, by a computer, a first set of nodes where each node in the first set corresponds to a unique individual present in the first set of genealogical data, each node comprising an identifier corresponding to a location of the unique individual within the first set of genealogical data;

create, by a computer, a second set of nodes where each node in the second set corresponds to a unique individual present in the second set of genealogical data, each node comprising an identifier corresponding to a location of the unique individual within the second set of genealogical data, the first and second sets of nodes having at least one unique individual in common;

concatenate, by the computer, the first set of nodes with the second set of nodes to create a concatenated set of nodes, the concatenating comprising merging nodes both comprising a same identifier;

select, by the computer from one of the nodes in the concatenated set, a common ancestor of the first human individual and the second human individual; and provide, by the computer, bibliographic data about the common ancestor to the first human individual.

10. The medium of claim 9 wherein the set of genetic data received from the first human individual includes values of single nucleotide polymorphisms present within DNA of the first human individual.

11. The medium of claim 9 wherein identifying shared segments of genetic data between the indicated one or more human individuals and the first human individual further comprises:
identifying a length of the shared segments of genetic data, wherein the length of the shared segments is a number of continuous based pairs that are identical between individuals; and
determining that the length of the shared segments exceeds a threshold length.

12. The medium of claim 9 wherein the first set of genealogical data describes familial relationships of the first human individual received from the first individual and the second set of genealogical data describes familial relationships of the second human individual received from the second individual.

13. The medium of claim 12 further comprising:
identifying by the computer, based on the described familial relationships of the first set of genealogical data, an additional individual identified in the first set of genealogical data genealogically related to the second human individual, the additional individual not identified in the second set; and
providing, by the computer, information about the additional individual to the second human individual.

14. The medium of claim 13 further comprising:
adding, by the computer, a record indicator of the additional individual to the second set of genealogical data in response to a request from the second individual.

15. The medium of claim 9 wherein the bibliographic data includes places of residence of the individuals.

16. The medium of claim 9 wherein the first human individual and the second human individual were unknown to each other prior to the step identifying segments of genetic data.

17. A computer system comprising:
a DNA data store configured to:

maintain a plurality of sets of genetic data sampled from a plurality of human individuals;
receive a set of genetic data sampled from a first human individual not included in the plurality of human individuals;
a DNA relationship engine configured to:
identify segments of genetic data shared between the received set of genetic data and one or more of the maintained sets of genetic data, the segmental sharing indicating that one or more human individuals corresponding to the one or more sets, including a second human individual, are genetically related to the first human individual;
a trees MRCA service configured to:
access a first set of genealogical data representing ancestors of the first human individual;
access a second set of genealogical data representing ancestors of the second human individual;
a hints engine configured to:
create, by a computer, a first set of nodes where each node in the first set corresponds to a unique individual present in the first set of genealogical data, each node comprising an identifier corresponding to a location of the unique individual within the first set of genealogical data;
create, by a computer, a second set of nodes where each node in the second set corresponds to a unique individual present in the second set of genealogical data, each node comprising an identifier corresponding to a location of the unique individual within the second set of genealogical data, the first and second sets of nodes having at least one unique individual in common;
concatenate, by the computer, the first set of nodes with the second set of nodes to create a concatenated set of nodes, the concatenating comprising merging nodes both comprising a same identifier;
select, by the computer from one of the nodes in the concatenated set, a common ancestor of the first human individual and the second human individual; and
provide, by the computer, bibliographic data about the common ancestor to the first human individual.

18. The system of claim 17 wherein the set of genetic data received from the first human individual includes values of single nucleotide polymorphisms present within DNA of the first human individual.

19. The system of claim 17 wherein identifying shared segments of genetic data between the indicated one or more human individuals and the first human individual further comprises:
identifying a length of the shared segments of genetic data, wherein the length of the shared segments is a number of continuous based pairs that are identical between individuals; and
determining that the length of the shared segments exceeds a threshold length.

20. The system of claim 17 wherein the first set of genealogical data describes familial relationships of the first human individual received from the first individual and the second set of genealogical data describes familial relationships of the second human individual received from the second individual.

21. The system of claim 20 wherein the trees MRCA engine is further configured to:
identify based on the described familial relationships of the first set of genealogical data, an additional individual identified in the first set of genealogical data genealogically related to the second human individual, the additional individual not identified in the second set; and
provide information about the additional individual to the second human individual.

22. The system of claim 21 wherein the trees MRCA engine is further configured to:
add a record indicator of the additional individual to the second set of genealogical data in response to a request from the second individual.

23. The system of claim 17 wherein the bibliographic data includes places of residence of the individuals.

24. The system of claim 17 wherein the first human individual and the second human individual were unknown to each other prior to the step identifying segments of genetic data.

* * * * *

UNITED STATES PATENT AND TRADEMARK OFFICE
CERTIFICATE OF CORRECTION

PATENT NO.       : 10,296,710 B2
APPLICATION NO.  : 15/182787
DATED            : May 21, 2019
INVENTOR(S)      : Barber et al.

It is certified that error appears in the above-identified patent and that said Letters Patent is hereby corrected as shown below:

In the Claims

Column 8, Line 63, Claim 1, delete "by a computer" and insert --by the computer--

Signed and Sealed this
Twelfth Day of November, 2019

Andrei Iancu
*Director of the United States Patent and Trademark Office*